(12) United States Patent
Aiki et al.

(10) Patent No.: US 6,768,311 B2
(45) Date of Patent: Jul. 27, 2004

(54) ION MEASURING DEVICE

(75) Inventors: Yoshiaki Aiki, Tokyo (JP); Wakao Sakamoto, Aomori (JP)

(73) Assignee: Andes Electric Co., Ltd., Hachinohe (JP)

( * ) Notice: Subject to any disclaimer, the term of this patent is extended or adjusted under 35 U.S.C. 154(b) by 50 days.

(21) Appl. No.: 10/173,762

(22) Filed: Jun. 19, 2002

(65) Prior Publication Data

US 2003/0006778 A1 Jan. 9, 2003

(30) Foreign Application Priority Data

Jun. 29, 2001 (JP) ........................................ 2001-197787

(51) Int. Cl.[7] ................................................ G01N 27/62
(52) U.S. Cl. ........................................ 324/464; 324/459
(58) Field of Search ................................ 324/464, 465, 324/459, 72.1, 72; 250/281

(56) References Cited

U.S. PATENT DOCUMENTS 4,812,711 A * 3/1989 Torok et al. ............ 315/111.91
5,059,803 A * 10/1991 Kronenberg ............. 250/385.1
5,506,507 A * 4/1996 Schwierzke et al. ........ 324/464
5,587,581 A * 12/1996 Stroosnyder ................ 250/287

* cited by examiner

Primary Examiner—N. Le
Assistant Examiner—John Teresinski
(74) Attorney, Agent, or Firm—Wenderoth, Lind & Ponack, L.L.P.

(57) ABSTRACT

The ion measuring device comprises an ion detector including a charge collector electrode disposed in an air passage with an air passing member provided therein and capable of collecting ions in air in the air passage and repelling electrodes disposed to face the charge collector electrode, a measurement computation device for executing computation processing on related to the charge on the charge collector electrode to obtain data representing the numbers of measured positive and negative ions per unit time and unit volume, a charging circuit including a switch for switching the positive and negative polarities of the charge applied to the repelling electrodes such that the repelling electrodes are charged to the same polarity as the polarity of measurement subject ions, and a discharging circuit for discharging the charge collector electrode at time intervals corresponding to the timings of switching by the switch.

2 Claims, 2 Drawing Sheets

ION MEASURING DEVICE

BACKGROUND OF THE INVENTION

1. Field of the Invention

This invention relates to ion measuring devices for measuring positive and negative ions as charged gas molecules or fine particles present in air.

2. Prior Art

Up to date, negative ions which are capable of giving good influence to the living body, such as healthy effect of preventing oxidization of the human body, effect of holding freshness of foodstuff and deodorizing effect, and also positive ions which provide converse action to negative ions, are attracting attention, and various types of ion measuring devices for measuring negative and/or positive ions are present.

In the prior art ion measuring devices, however, a positive ion measuring unit for measuring positive ions and a negative ion measuring unit for measuring negative ions are present independently, or a single ion measuring unit has independent negative and positive ion measuring parts. Therefore, the prior art ion measuring devices are inevitably large in scale and expensive. Besides, although air ions require fine and sophisticated measuring conditions, it has been very doubtful that negative and positive ion measurement values obtained by different measuring systems are in right correlation to one another. In the prior art, an ion measuring device is also present, in which the negative and positive ion measurements are made in a single system by switching one over to the other. In this case, however, the switching of the "negative" and "positive" measurements is done manually, and it is necessary to manually discharge a charge collector in a measuring part whenever the switching is done. Therefore, the operation is cumbersome, and the measurement requires great labor and time.

SUMMARY OF THE INVENTION

The invention has an object of providing an ion measuring device, which can accurately and readily measure both positive and negative ion data and be realized as a reduced size and thickness structure. To attain this object, an ion measuring device is provided, which comprises an ion detecting means including a charge collector electrode disposed in an air passage with an air passing member disposed therein and capable of collecting ions in air and repelling electrodes disposed to face the charge collector electrode, a measurement computation means for measuring charge on the charge collector electrode and executing computation processing on the measured charge to obtain data representing the number of measured positive and negative ions per unit time and unit volume, a charging means including a switching means for switching the positive and negative polarities of charging the repelling electrodes such that the repelling electrodes are charged to the same polarity of measurement subject ions, and a discharging means for discharging the charge collector electrode at time intervals corresponding to the timings of switching by the switching means.

DETAILED DESCRIPTION OF THE PREFERRED EMBODIMENTS

Figure 1:
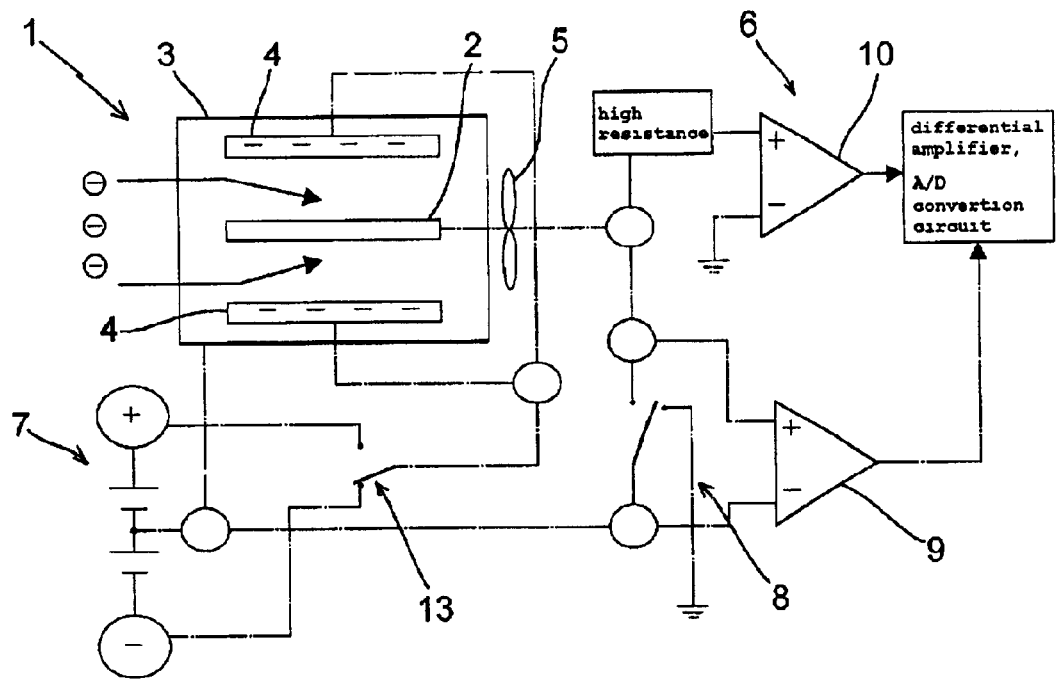
FIG. 1 is a schematic showing an ion measuring device.

FIG. 1 is a schematic showing an ion measuring device according to the invention. The illustrated ion measuring device 1 comprises a charge collector electrode 2 which are charged when struck by ions in air, an air passage 3, which surrounds the charge collector electrode 2 and passes air through it, a repelling electrode 4 disposed at a distance from and face-to-face with the opposite surfaces of the charge collector electrode 2, an air passing member 5 including a motor-driven fun fan for passing air through the air passage 3, a measurement computation means 6 for detecting and making computations on related to the charge on the charged charge collector electrode 2, a charging means 7 for positively or negatively charging the repelling electrodes 4, and a discharging means 8 including a relay switch for being grounded to cause discharge of the charged charge collector electrode 2.

Figure 2:
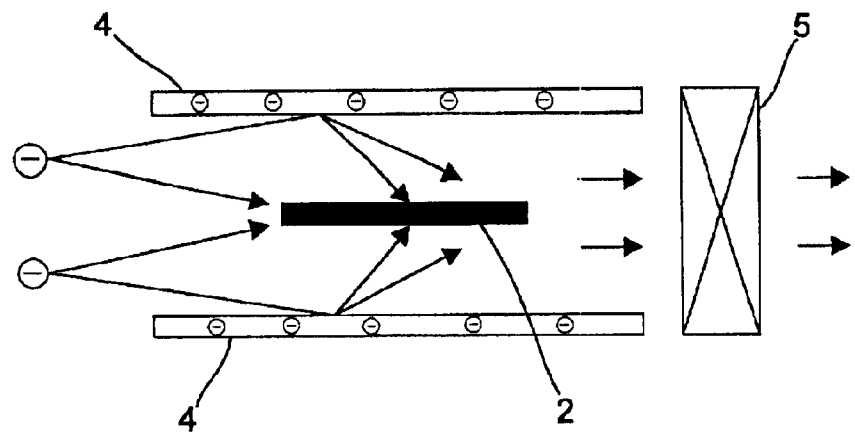
FIG. 2 is a view for explaining a charge collector electrode and pair repelling electrodes in the ion measuring device according to the invention.

FIG. 2 illustrates the function of the charge collector electrode 2 and the repelling electrodes 4 in the ion measuring device 1. The device 1 is in the illustrated state for measuring negative ions in air. The repelling electrodes 4 are held negatively charged by the charging means 7, and air containing negative ions is introduced into the air passage 3 with fixed rate rotation of the air passing means 5. Since the repelling electrodes 4 are held negatively charged, negative ions approaching the repelling electrodes 4 are repelled toward, strike, and are collected by the charge collector electrode 2. Positive ions in air, on the other hand, are attracted to and neutralized by the repelling electrodes 4.

Figure 4:
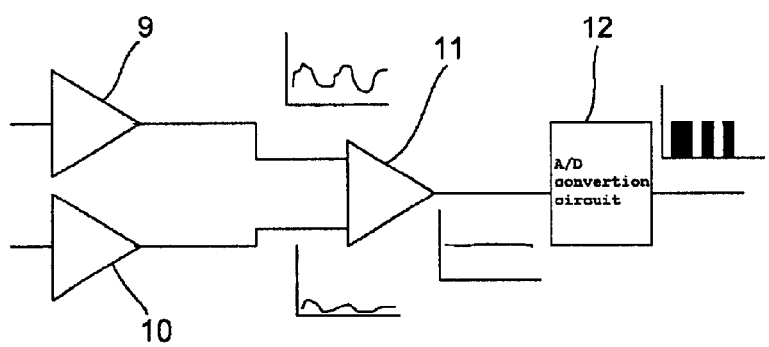
FIG. 4 is a schematic for explaining a measurement computation means in the ion measuring device according to the invention.

As shown in FIG. 4, the charge on the charge collector electrode 2, which has been charged by being struck by negative ions, are fed to an ion voltage detecting amplifier 9 and also through a high resistance to a noise detecting amplifier 10. For subtracting a periodic and steady-state noise component (such as hum noise, etc.) the two amplifier outputs are fed to a differential amplifier 11. The output of the amplifier 11 is fed to an analog-to-digital conversion circuit 12 for conversion to digital data.

Figure 3:
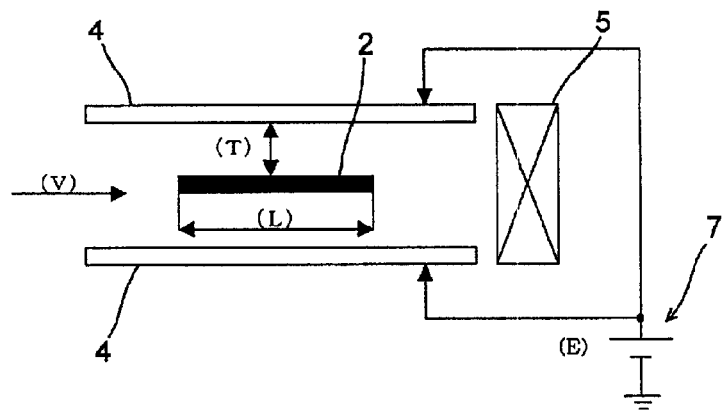
FIG. 3 is a view showing design values of the ion measuring device according to the invention.

Air ions, from the electric nature thereof, are moved under influence of an electric field, and the velocity of motion is proportional to the electric field intensity. The velocity of motion per unit electric field (1 V/m) is called mobility. The mobility of air ions is determined by the ratio between the quantity of electricity and the mass of the ions. Ions with high mobility are called small ions, and those with low mobility are called large ions. The small ions are thought to have good influence on the living body, and they result from charging of gas molecules (such as oxygen molecules). Positive ions usually have a mobility of 1.36 cm/sec., while negative ions usually have a mobility of about 2.1 cm/sec. The large ions result from attachment of dust particles or other fine particles to small ions or electrons, and their mobility is as low as about 0.0005 to 0.01 cm/sec. This embodiment of the ion measuring device 1 is designed to measure small ions. Referring to FIG. 3, the mobility of small ions is set as in the following Equation (1).

$$\text{Mobility}\left(\frac{\text{cm}}{\text{sec}} / \frac{V}{\text{cm}}\right) = \frac{V \times T}{L \times \frac{E}{T}} \qquad <\text{Equation (1)}>$$

where V is the air passage rate, T is the distance between the charge collector electrode 2 and each repelling electrode 4, L is the length of the charge collector electrode 2, and E is the potential on the repelling electrodes 4.

Figure 5:
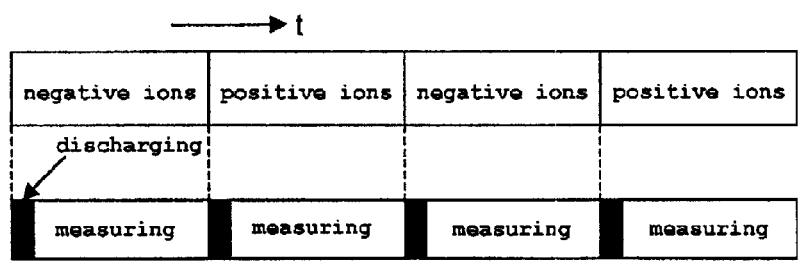
FIG. 5 is a view for describing a time chart of measurement in the ion measuring device according to the invention.

FIG. 5 shows a time chart for measuring negative and positive ion data in the ion measuring device by switching the two measurements one over to the other, (i.e. alternating the measurement of negative ion data and the measurement of positive ion data). Specifically, the negative and positive ion data measurements are alternately switched for every one second. In the specific method, the charged charge collector electrode 2 is discharged by grounding the same (to the device ground or the like) by turning on the discharging means, while the repelling electrodes 4 are charged to negative potential by switching the switching means 13, i.e., the relay switch, in the charging means 7 to the power supply side, i.e., to the same (negative) polarity as the polarity of the measurement subject ions. Then, the discharging means 8 is turned off to start charge collection on the charge collector electrode 2, while the noise potential with respect to the ground potential of the device is detected by feeding the output of the charge collector electrode 2 through the high resistance to the noise detecting amplifier 10. The ion voltage detecting amplifier 9 converts the quantity of charge on the charge collector electrode 2 to a voltage signal. The differential amplifier 11 removes noise component as the output of the noise detecting amplifier 10 from the output of the amplifier 9, and its output is fed to the analog-to-digital converter circuit 12 for processing therein as digital signal. The circuit 12 outputs data representing the number of negative ions per unit time and unit volume, the output data being fed to a display means or the like.

When this measurement has been continued for a predetermined time, for instance one second, the positive ion data measurement is subsequently executed. Specifically, the charged charge collector electrode 2 is discharged by grounding it by turning on the discharging means 8, while the repelling electrodes 4 are charged to positive potential by switching the switching means 13 of the charging means 7 to the positive power supply side. Then, the discharging means 8 is turned off to start charge collection on the charge collector electrode 2, while the noise potential with respect to the ground potential of the device is detected by feeding the output of the charge collector electrode 2 through the high resistance to the noise detecting amplifier 10. The ion voltage detecting amplifier 9 converts the quantity of charge on the charge collector electrode 2 to a voltage signal. The differential amplifier 11 removes the noise component as the output of the noise detecting amplifier 10 from the output of the amplifier 9. The analog-to-digital converter circuit 12 converts the output of the differential amplifier 11 to digital signal, which is fed as data representing the number of positive ions per unit time and unit volume to the display means or the like. As has been shown, the negative and positive ion data measurements can be automatically alternatively switched in the same measuring system.

As has been described in the foregoing, with the ion measuring device according to the invention both the negative and positive ion data measurements are made in the same measuring system. Thus, it is possible to obtain in data measurement values, which are sufficiently correlative, accurate and reliable. In addition, since the switched positive and negative ion data measurements and discharging of the charge collector electrode are automatically done, the ion measurement can be readily obtained without involving any cumbersome operation.

Furthermore, since the measurement computation means executes the computation process by removing noise data from the charge measurement data from the charge collector electrode, it is possible to obtain accurate ion measurement free from error generation due to noise component.

What is claimed is:

1. An ion measuring device comprising:
   an ion detector including
      a charge collector electrode disposed in an air passage and operable to collect ions in air in the air passage,
      repelling electrodes disposed to face said charge collector electrode;
   a measurement computer operable to perform alternative measurement of positive and negative charge quantities on said charge collector electrode and respectively compute positive and negative ion number data from the alternatively measured positive and negative charge quantities;
   a charger operable to charge the repelling electrodes, said charger including a switch operable to switch a polarity of the charge of the repelling electrodes to positive or negative polarity such that the repelling electrodes are charged to the same polarity as the polarity of the alternative measurement of charge quantities by said measurement computer;
   a discharger including a relay switch operable to discharge said charge collector electrode to ground at time intervals corresponding to a timing of switching by said switch of said charger.

2. The ion measuring device according to claim 1, wherein said measurement computer is operable to remove noise from data obtained by the alternative measurement of positive and negative charge quantities on said charge collector electrode.

* * * * *